United States Patent
Berghaus et al.

(10) Patent No.: US 8,778,840 B2
(45) Date of Patent: Jul. 15, 2014

(54) SOLUBLE LIQUID FORMULATIONS OF QUINCLORAC AMMONIUM SALTS

(75) Inventors: Rainer Berghaus, Speyer (DE); Terrance Cannan, Raleigh, NC (US); Joseph Zawierucha, Cary, NC (US); Glenn W. Oliver, Apex, NC (US)

(73) Assignee: BASF SE, Ludwigshafen (DE)

( * ) Notice: Subject to any disclaimer, the term of this patent is extended or adjusted under 35 U.S.C. 154(b) by 313 days.

(21) Appl. No.: 12/669,198

(22) PCT Filed: Jul. 7, 2008

(86) PCT No.: PCT/EP2008/058801
§ 371 (c)(1),
(2), (4) Date: Jun. 7, 2010

(87) PCT Pub. No.: WO2009/013120
PCT Pub. Date: Jan. 29, 2009

(65) Prior Publication Data
US 2010/0255992 A1 Oct. 7, 2010

Related U.S. Application Data

(60) Provisional application No. 60/951,324, filed on Jul. 23, 2007.

(51) Int. Cl.
*A01N 43/42* (2006.01)
*A01N 25/02* (2006.01)
*C07D 215/48* (2006.01)

(52) U.S. Cl.
USPC ........... 504/247; 514/299; 514/311; 546/152; 546/170; 562/400; 562/405; 562/491; 562/622

(58) Field of Classification Search
USPC ........... 504/247; 514/299, 311; 562/400, 405, 562/491, 622; 546/152, 170
See application file for complete search history.

(56) References Cited

U.S. PATENT DOCUMENTS

| 4,497,651 A | 2/1985 | Hagen et al. |
| 8,232,230 B2 * | 7/2012 | Volgas et al. ................. 504/130 |

FOREIGN PATENT DOCUMENTS

| WO | WO 99/00012 | 1/1999 |
| WO | WO 99/00012 A | * 1/1999 |
| WO | WO99/00012 A1 | * 1/1999 |
| WO | WO 03/103396 | 12/2003 |
| WO | WO 03/103396 A1 | * 12/2003 ............. A01N 39/04 |
| WO | WO 03/103396 A1 | * 12/2003 ............. A01N 43/40 |
| WO | WO03/103396 A1 | * 12/2003 ............. A01N 43/40 |

OTHER PUBLICATIONS

"Ethoxylation" Wikipedia [online], 2007 and 1934 [retrieved Apr. 19, 2012] Retrieved from the Internet: <URL: http://en.wikipedia.org/wiki/Ethoxylation>.*
"Ethoxylation" Wikipedia [online], [retrieved Apr. 19, 2012] Retrieved from the Internet: en.wikipedia.org/wiki/Ethoxylation.*
International Search Report completed Jan. 30, 2009, in International Application No. PCT/EP2008/058801, filed Jul. 7, 2008.
International Preliminary Report on Patentability dated Jan. 26, 2010, from corresponding International Application No. PCT/EP2008/058801, filed Jul. 7, 2008.

* cited by examiner

Primary Examiner — Jane C Oswecki
(74) Attorney, Agent, or Firm — Brinks Gilson & Lione

(57) ABSTRACT

The present invention relates to novel soluble liquid (SL) formulations comprising
A) quinclorac ammonium salts of formula I

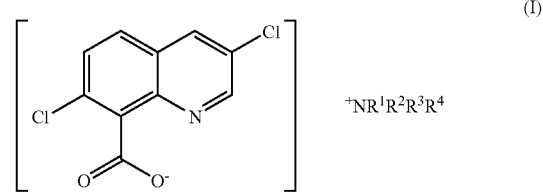

wherein
$R^1, R^2, R^3$ and $R^4$ are independently hydrogen or optionally substituted alkyl,
and
B) a solvents of formula IIa

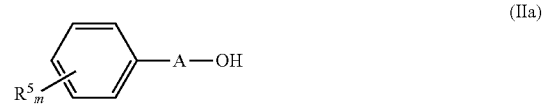

wherein
$R^5$ is alkyl;
A is alkylene or oxyalkylene; and
m is 0, 1, 2 or 3;
and/or
a solvent of formula IIb

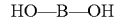

wherein
B is a straight-chain or branched alkylene or alkyleneoxyalkylene or alkyleneoxyalkyleneoxyalkylene.

33 Claims, No Drawings

SOLUBLE LIQUID FORMULATIONS OF QUINCLORAC AMMONIUM SALTS

This application is a National Stage application of International Application No. PCT/EP2008/058801, filed Jul. 7, 2008, which claims the benefit of U.S. Provisional Application No. 60/951,324, filed Jul. 23, 2007, the entire contents of which is hereby incorporated herein by reference.

The present invention relates to novel soluble liquid formulations having herbicidal activity and more specifically relates to a novel herbicidally active soluble liquid formulation of ammonium salts of quinclorac in a suitable solvent. The invention further relates to methods for controlling undesired plant growth.

Quinclorac (3,7-dichloro-8-quinolinecarboxylic acid) is a known herbicide. Due to its low solubility in water (0.065 mg/kg at pH 7 at 20° C.) it is usually formulated in a solid form. However, liquid formulations are sought showing an improved solubility of quinclorac and/or improved herbicidal activity.

It is therefore an object of the present invention to create a liquid formulation having herbicidal activity by increasing the solubility of quinclorac.

It has been found, surprisingly, that soluble liquid (SL) formulations comprising A) quinclorac ammonium salts of formula I

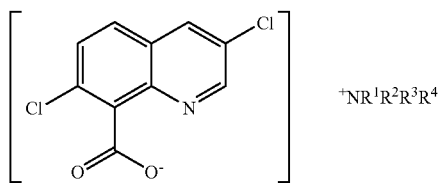

(I)

wherein $R^1$, $R^2$, $R^3$ and $R^4$ are independently hydrogen, $C_1$-$C_6$-alkyl, —(CHR$^a$—CHR$^b$—Z$_1$)$_x$—H or —(CHR$^a$—CHR$^b$—CHR$^c$—CHR$^d$—Z$_2$)$_y$—H (wherein R$^a$, R$^b$, R$^c$ and R$^d$ are independently hydrogen or $C_1$-$C_6$-alkyl, wherein $Z_1$ and $Z_2$ are independently O, NH or N—$C_1$-$C_6$-alkyl, and wherein x and y are independently an integer from 1 to 6);

and

B) a solvents of formula IIa

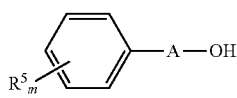

(IIa)

wherein $R^5$ is $C_1$-$C_6$-alkyl;

A is $C_1$-$C_6$-alkylene or $C_1$-$C_6$-oxyalkylene; and m is 0, 1, 2 or 3;

and/or a solvent of formula IIb

HO—B—OH (IIb)

wherein

B is a straight-chain or branched $C_2$-$C_8$-alkylene or $C_2$-$C_4$-alkyleneoxy-$C_2$-$C_4$-alkylene or $C_2$-$C_3$-alkyleneoxy-$C_2$-$C_3$-alkyleneoxy-$C_2$-$C_3$-alkylene;

achieve these objectives.

The solvents of formula IIa and/or IIb provide adequate solubility of the quinclorac ammonium salts of formula I. Moreover, the use of the solvents of formula IIa and/or IIb has been found to result in very good stability of the quinclorac ammonium salts of formula I in solution. In addition the herbicidal activity of these liquid formulations is increased.

In a preferred embodiment of the invention the SL formulation comprises as component A) a quinclorac ammonium salt wherein $R^1$ is hydrogen or $C_1$-$C_6$-alkyl;
$R^2$, $R^3$ are independently $C_1$-$C_6$-alkyl;
$R^4$ is hydrogen.

In another preferred embodiment of the invention the SL formulation comprises as component A) a quinclorac ammonium salt wherein $R^1$ is hydrogen, methyl or ethyl;
$R^2$, $R^3$ are independently methyl or ethyl;
$R^4$ is hydrogen.

In another preferred embodiment of the invention the SL formulation comprises as component A) a quinclorac ammonium salt wherein $R^1$, $R^4$ are hydrogen;
$R^2$, $R^3$ are independently $C_1$-$C_6$-alkyl.

In another preferred embodiment of the invention the SL formulation comprises as component A) a quinclorac ammonium salt wherein $R^1$, $R^4$ are hydrogen;
$R^2$, $R^3$ are independently methyl or ethyl.

In another preferred embodiment of the invention the SL formulation comprises as component A) quinclorac dimethylammonium.

In another preferred embodiment of the invention the SL formulation comprises as component A) a quinclorac ammonium salt wherein $R^1$ is hydrogen or $C_1$-$C_6$-alkyl;
$R^2$, $R^3$ are independently —(CHR$^a$—CHR$^b$—Z$_1$)$_x$—H or —(CHR$^a$—CHR$^b$—CHR$^c$—CHR$^d$—Z$_2$)$_y$—H (wherein R$^a$, R$^b$, R$^c$ and R$^d$ are independently hydrogen or $C_1$-$C_6$-alkyl, wherein $Z_1$ and $Z_2$ are independently O, NH or N—$C_1$-$C_6$-alkyl, and wherein x and y are independently an integer from 1 to 6);
$R^4$ is hydrogen.

In another preferred embodiment of the invention the SL formulation comprises as component A) a quinclorac ammonium salt wherein $R^1$ is hydrogen or $C_1$-$C_6$-alkyl;
$R^2$ is —(CHR$^a$—CHR$^b$—Z$_1$)$_x$—H or —(CHR$^a$—CHR$^b$—CHR$^c$—CHR$^d$—Z$_2$)$_y$—H, (wherein R$^a$, R$^b$, R$^c$ and R$^d$ are independently hydrogen or $C_1$-$C_6$-alkyl, wherein $Z_1$ and $Z_2$ are independently O, NH or N—$C_1$-$C_6$-alkyl, and wherein x and y are independently an integer from 1 to 6; preferably wherein $Z_1$ and $Z_2$ are O); especially —(CH$_2$—CH$_2$—O)$_x$—H or —(CH$_2$—CH$_2$—CH$_2$—CH$_2$—O)$_y$—H and wherein m and n are independently an integer from 1 to 6;
$R^3$, $R^4$ are hydrogen.

In another preferred embodiment of the invention the SL formulation comprises as component A) a quinclorac ammonium salt wherein $R^1$ is hydrogen, methyl or ethyl;
$R^2$ is $C_1$-$C_6$-hydroxyalkyl or $C_1$-$C_6$-hydroxyalkoxy-$C_1$-$C_6$-alkyl;
$R^3$, $R^4$ are hydrogen.

In another preferred embodiment of the invention the SL formulation comprises as component A) a quinclorac ammonium salt wherein
$R^1$, $R^3$, $R^4$ are hydrogen;
$R^2$ is 2-hydroxyethyl or 2-(2-hydroxyethoxy)ethyl.

In another preferred embodiment of the invention the SL formulation comprises as component A) a quinclorac ammonium salt wherein
$R^1$, $R^3$, $R^4$ are hydrogen;
$R^2$ is 2-(2-hydroxyethoxy)ethyl.

In another preferred embodiment of the invention the SL formulation comprises as component B) a solvent of formula IIa and/or a solvent of formula IIb.

In another preferred embodiment of the invention the SL formulation comprises as component B) only a solvent of formula IIa.

In another preferred embodiment of the invention the SL formulation comprises as component B) only a solvent of formula IIa and said solvent of formula IIa is characterized by
m is 0.

In another preferred embodiment of the invention the SL formulation comprises as component B) only a solvent of formula IIa and said solvent of formula IIa is characterized by:
A is $C_1$-$C_6$-alkylene or $C_1$-$C_6$-oxyalkylene;
m is 0.

In another preferred embodiment of the invention the SL formulation comprises as component B) only a solvent of formula IIa and said solvent of formula IIa is characterized by:
A is methylene, ethylene or oxyethylene;
m is 0.

In another preferred embodiment of the invention the SL formulation comprises as component B) only benzyl alcohol.

In another preferred embodiment of the invention the SL formulation comprises as component A) a quinclorac ammonium salt wherein
$R^1$, $R^4$ are hydrogen;
$R^2$, $R^3$ are independently $C_1$-$C_6$-alkyl;
and as component B) only a solvent of formula IIa and said solvent of formula IIa is characterized by:
A is $C_1$-$C_6$-alkylene or $C_1$-$C_6$-oxyalkylene;
m is 0.

In another preferred embodiment of the invention the SL formulation comprises as component A) a quinclorac ammonium salt wherein
$R^1$, $R^4$ are hydrogen;
$R^2$, $R^3$ are independently $C_1$-$C_6$-alkyl;
and as component B) only a solvent of formula IIa and said solvent of formula IIa is characterized by:
A is methylene, ethylene or oxyethylene;
m is 0.

In another preferred embodiment of the invention the SL formulation comprises as component A) quinclorac dimethylammonium and as component B) only benzyl alcohol.

In another preferred embodiment of the invention the SL formulation comprises as component A) a quinclorac ammonium salt wherein
$R^1$, $R^3$, $R^4$ are hydrogen;
$R^2$ is 2-hydroxyethyl or 2-(2-hydroxyethoxy)ethyl;
and as component B) only a solvent of formula IIa and said solvent of formula IIa is characterized by:
A is $C_1$-$C_6$-alkylene or $C_1$-$C_6$-oxyalkylene;
m is 0.

In another preferred embodiment of the invention the SL formulation comprises as component A) a quinclorac ammonium salt wherein $R^1$, $R^3$, $R^4$ are hydrogen;
$R^2$ is 2-hydroxyethyl or 2-(2-hydroxyethoxy)ethyl;
and as component B) only a solvent of formula IIa and said solvent of formula IIa is characterized by:
A is methylene, ethylene or oxyethylene;
m is 0.

In another preferred embodiment of the invention the SL formulation comprises as component A) quinclorac mono-[2 (2-hydroxyethoxy)-ethyl]-ammonium and as component B) only benzyl alcohol.

In another preferred embodiment of the invention the SL formulation comprises as component B) only a solvent of formula IIb.

In another preferred embodiment of the invention the SL formulation comprises as component B) only a solvent of formula IIb and said solvent of formula IIb is characterized by:
B is a straight-chain or branched $C_2$-$C_8$-alkylene or $C_2$-$C_4$-alkyleneoxy-$C_2$-$C_4$-alkylene.

In another preferred embodiment of the invention the SL formulation comprises as component B) a only solvent of formula IIb and said solvent of formula IIb is characterized by:
B is ethylene, propylene or ethyleneoxyethylene.

In another preferred embodiment of the invention the SL formulation comprises as component B) only glycol (HO—$CH_2CH_2$—OH).

In another preferred embodiment of the invention the SL formulation comprises as component A) a quinclorac ammonium salt wherein
$R^1$, $R^4$ are hydrogen;
$R^2$, $R^3$ are independently $C_1$-$C_6$-alkyl;
and as component B) only a solvent of formula IIb and said solvent of formula IIb is characterized by:
B is a straight-chain or branched $C_2$-$C_8$-alkylene or $C_2$-$C_4$-alkyleneoxy-$C_2$-$C_4$-alkylene.

In another preferred embodiment of the invention the SL formulation comprises as component A) a quinclorac ammonium salt wherein
$R^1$, $R^4$ are hydrogen;
$R^2$, $R^3$ are independently $C_1$-$C_6$-alkyl;
and as component B) only a solvent of formula IIb and said solvent of formula IIb is characterized by:
B is ethylene, propylene or ethyleneoxyethylene.

In another preferred embodiment of the invention the SL formulation comprises as component A) quinclorac dimethylammonium and as component B) only glycol.

In another preferred embodiment of the invention the SL formulation comprises as component A) a quinclorac ammonium salt wherein
$R^1$, $R^3$, $R^4$ are hydrogen;
$R^2$ is 2-hydroxyethyl or 2-(2-hydroxyethoxy)ethyl;
and as component B) only a solvent of formula IIb and solvent of formula IIb is characterized by:
B is a straight-chain or branched $C_2$-$C_8$-alkylene or $C_2$-$C_4$-alkyleneoxy-$C_2$-$C_4$-alkylene.

In another preferred embodiment of the invention the SL formulation comprises as component A) a quinclorac ammonium salt wherein
$R^1$, $R^3$, $R^4$ are hydrogen;
$R^2$ is 2-hydroxyethyl or 2-(2-hydroxyethoxy)ethyl;
and as component B) only a solvent of formula IIb and solvent of formula IIb is characterized by:
B is ethylene, propylene or ethyleneoxyethylene.

In another preferred embodiment of the invention the SL formulation comprises as component A) quinclorac mono-[2 (2-hydroxyethoxy)-ethyl]-ammonium and as component B) only glycol.

In another preferred embodiment of the invention the SL formulation comprises as component B) a solvent of formula IIa and a solvent of formula IIb.

In another preferred embodiment of the invention the SL formulation comprises as component B) a solvent of formula IIa wherein m=0, and a solvent of formula IIb wherein:
B is a straight-chain or branched $C_2$-$C_8$-alkylene or $C_2$-$C_4$-alkyleneoxy-$C_2$-$C_4$-alkylene.

In another preferred embodiment of the invention the SL formulation comprises as component B) a solvent of formula IIa and said solvent of formula IIa wherein:
A is $C_1$-$C_8$-alkylene or $C_1$-$C_8$-oxyalkylene;
m is 0;
and a solvent of formula IIb and said solvent wherein
B is ethylene, propylene or ethyleneoxyethylene.

In another preferred embodiment of the invention the SL formulation comprises as component B) benzyl alcohol and glycol.

In another preferred embodiment of the invention the SL formulation comprises as component A) a quinclorac ammonium salt wherein
$R^1$, $R^4$ are hydrogen;
$R^2$, $R^3$ are independently $C_1$-$C_8$-alkyl;
and as component B) benzyl alcohol and glycol.

In another preferred embodiment of the invention the SL formulation comprises as component A) quinclorac dimethylammonium and as component B) benzyl alcohol and glycol.

In another preferred embodiment of the invention the SL formulation comprises as component A) a quinclorac ammonium salt wherein
$R^1$, $R^3$, $R^4$ are hydrogen;
$R^2$ is 2-hydroxyethyl or 2-(2-hydroxyethoxy)ethyl;
and as component B) benzyl alcohol and glycol.

In another preferred embodiment of the invention the SL formulation comprises as component A) quinclorac mono-[2 (2-hydroxyethoxy)-ethyl]-ammonium and as component B) benzyl alcohol and glycol.

In another preferred embodiment of the invention the SL formulation comprises beneath the components A) and B) one or more additional herbicidal active ingredients.

Suitable additional herbicidal active ingredients are auxin herbicides, especially like clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, clopyralid, fluoroxypyr, picloram, triclopyr or benazolin or one of its environmentally compatible salts, esters and amides.

Other suitable additional herbicidal active ingredients are benzothiadiazole-type herbicides, like bentazon or one of its environmentally compatible salts, or imidazolinone-type herbicides, like imazapic, imazapyr, imazaquin, imazethapyr or imazamox, or one of their environmentally compatible salts.

In an especial embodiment of the invention the SL formulation comprises beneath the components A) and B) one additional herbicidal active ingredients.

Preferably the additional herbicidal active ingredient is an auxin herbicide, especially like clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, clopyralid, fluroxypyr, picloram, trichlopyr or benazolin or one of its environmentally compatible salts, esters and amides.

In another preferable embodiment the additional herbicidal active ingredient is selected from 2,4-D, dichlorprop, dichlorprop-P, MCPA, mecoprop, mecoprop-P and dicamba, especially from 2,4-D, MCPA, mecoprop, mecoprop-P, dicamba, clopyralid, fluoroxypyr and triclopyr or one of its environmentally compatible salts, esters and amides.

In another preferable embodiment the additional herbicidal active ingredient is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferable embodiment the additional herbicidal active ingredient is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium.

In another preferable embodiment the additional herbicidal active ingredient is selected from triclopyr, fluoroxypyr or clopyralid or one of its environmentally compatible salts, esters and amids.

In another preferable embodiment the additional herbicidal active ingredient is bentazon, imazapic, imazapyr, imazaquin, imazethapyr or imazamox, or one of its environmentally compatible salts, especially bentazon or one of its environmentally compatible salts.

In an especial embodiment of the invention the SL formulation comprises beneath the components A) and B) two or more additional herbicidal active ingredients, preferably two additional herbicidal active ingredients.

Preferably at least one of the additional herbicidal active ingredients is an auxin herbicide, especially one like clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, clopyralid, fluoroxypyr, picloram, trichlopyr or benazolin or one of its environmentally compatible salts, esters and amides.

In another preferable embodiment at least one of the additional herbicidal active ingredients is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides.

In another preferable embodiment at least one of the additional herbicidal active ingredient is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferable embodiment the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferable embodiment the first of the two or more, preferably two, additional herbicidal active ingredients is selected from dicamba, dicamba dimethylammonium, dicamba diolamine, dicamba potassium, dicamba mono-[2(2-hydroxyethoxy)ethyl]-ammonium and dicamba sodium and the second of the two and more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium.

In another preferable embodiment the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two and more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium.

In another preferable embodiment at least one of the additional herbicidal active ingredients is selected from clopyralid, fluoroxypyr and triclopyr, or one of its environmentally compatible salts, esters and amides.

In another preferable embodiment at least one of the additional herbicidal active ingredients is bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac dimethylammonium, as component B) benzyl alcohol and one or more additional herbicidal active ingredients.

In another preferred embodiment of the invention the SL formulation comprises as component A) quinclorac dimethylammonium, as component B) benzyl alcohol and one additional herbicidal active ingredient.

In another preferred embodiment of the invention the SL formulation comprises as component A) quinclorac dimethylammonium, as component B) benzyl alcohol and one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) benzyl alcohol and one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) benzyl alcohol and one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine.

In another preferred embodiment of the invention the SL formulation comprises as component A) quinclorac dimethylammonium, as component B) benzyl alcohol and one additional herbicidal active ingredient which is selected from clopyralid, fluoroxypyr and triclopyr, or one of its environmentally compatible salts, esters and amides.

In another preferred embodiment of the invention the SL formulation comprises as component A) quinclorac dimethylammonium, as component B) benzyl alcohol and one additional herbicidal active ingredient which is selected from bentazon, imazapic, imazapyr, imazaquin, imazethapyr or imazamox, or one of its environmentally compatible salts, especially bentazon or one of its environmentally compatible salts In another preferred embodiment of the invention the SL formulation comprises as component A) quinclorac dimethylammonium, as component B) benzyl alcohol and two or more, preferably two, additional herbicidal active ingredients.

In another preferred embodiment of the invention the SL formulation comprises as component A) quinclorac dimethylammonium, as component B) benzyl alcohol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) benzyl alcohol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) benzyl alcohol and two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac dimethylammonium, as component B) benzyl alcohol and two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P.

In another preferred embodiment of the invention the SL formulation comprises as component A) quinclorac dimethylammonium, as component B) benzyl alcohol and two or more, preferably two additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium.

In another preferred embodiment of the invention the SL formulation comprises as component A) quinclorac dimethylammonium, as component B) benzyl alcohol and two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides.

In another preferred embodiment of the invention the SL formulation comprises as component A) quinclorac dimethylammonium, as component B) benzyl alcohol and two or more, preferably two, additional herbicidal active ingredients wherein the first of the two or more, preferably two, additional herbicidal active ingedients is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac dimethylammonium, as component B) glycol and one or more additional herbicidal active ingredients.

In another preferred embodiment of the invention the SL formulation comprises as component A) quinclorac dimethylammonium, as component B) glycol and one additional herbicidal active ingredient.

In another preferred embodiment of the invention the SL formulation comprises as component A) quinclorac dimethylammonium, as component B) glycol and one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) glycol and one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) glycol and one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine.

In another preferred embodiment of the invention the SL formulation comprises as component A) quinclorac dimethylammonium, as component B) glycol and one additional herbicidal active ingredient which is selected from is selected from clopyralid, fluoroxypyr and triclopyr, or one of its environmentally compatible salts, esters and amides.

In another preferred embodiment of the invention the SL formulation comprises as component A) quinclorac dimethylammonium, as component B) glycol and one additional herbicidal active ingredient which is bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac dimethylammonium, as component B) glycol and two or more, preferably two, additional herbicidal active ingredients.

In another preferred embodiment of the invention the SL formulation comprises as component A) quinclorac dimethylammonium, as component B) glycol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) glycol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) glycol and two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac dimethylammonium, as component B) glycol and two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P.

In another preferred embodiment of the invention the SL formulation comprises as component A) quinclorac dimethylammonium, as component B) glycol and two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium.

In another preferred embodiment of the invention the SL formulation comprises as component A) quinclorac dimethylammonium, as component B) glycol and two or more, preferably two, additional herbicidal active ingredient wherein the first of the two or more, preferably two, additional herbicidal active ingredients is selected from clopyralid, fluoroxypyr and triclopyr, or one of its environmentally compatible salts, esters and amides.

In another preferred embodiment of the invention the SL formulation comprises as component A) quinclorac dimethylammonium, as component B) glycol and two or more, preferably two, additional herbicidal active ingredient wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac dimethylammonium, as component B) benzyl alcohol and glycol and one or more additional herbicidal active ingredients.

In another preferred embodiment of the invention the SL formulation comprises as component A) quinclorac dimethylammonium, as component B) benzyl alcohol and glycol and one additional herbicidal active ingredient.

In another preferred embodiment of the invention the SL formulation comprises as component A) quinclorac dimethylammonium, as component B) benzyl alcohol and glycol and one additional herbicidal active ingredient which is selected from 2,4-D, dichlorprop, dichlorprop-P, MCPA, mecoprop, mecoprop-P, dicamba, clopyralid, fluroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) benzyl alcohol and glycol and one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) benzyl alcohol and glycol and one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine.

In another preferred embodiment of the invention the SL formulation comprises as component A) quinclorac dimethylammonium, as component B) benzyl alcohol and glycol and one additional herbicidal active ingredient which is selected from is selected from clopyralid, fluoroxypyr and triclopyr, or one of its environmentally compatible salts, esters and amides.

In another preferred embodiment of the invention the SL formulation comprises as component A) quinclorac dimethylammonium, as component B) benzyl alcohol and glycol and one additional herbicidal active ingredient which is selected from bentazon, imazapic, imazapyr, imazaquin, imazethapyr or imazamox, or one of its environmentally compatible salts, especially bentazon or one of its environmentally compatible salts In another preferred embodiment of the invention the SL formulation comprises as component A) quinclorac dimethylammonium, as component B) benzyl alcohol and glycol and two or more, preferably two, additional herbicidal active ingredients.

In another preferred embodiment of the invention the SL formulation comprises as component A) quinclorac dimethylammonium, as component B) benzyl alcohol and glycol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac dimethylammonium, as component B) benzyl alcohol and glycol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium.

In another preferred embodiment of the invention the SL formulation comprises as component A) quinclorac dimethylammonium, as component B) benzyl alcohol and glycol and two or more, preferably two, additional herbicidal active ingredients wherein the first of the two or more, preferably two, additional herbicidal active ingredient is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac dimethylammonium, as component B) benzyl alcohol and glycol and two or more, preferably two, additional herbicidal active ingredients wherein the first of the two or more, preferably two, additional herbicidal active ingredient is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P.

In another preferred embodiment of the invention the SL formulation comprises as component A) quinclorac dimethylammonium, as component B) benzyl alcohol and glycol and two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium.

In another preferred embodiment of the invention the SL formulation comprises as component A) quinclorac dimethylammonium, as component B) benzyl alcohol and glycol and two or more, preferably two, additional herbicidal active ingredients wherein the first of the two or more, preferably two, additional herbicidal active ingredients is selected from clopyralid, fluroxypyr and triclopyr, or one of its environmentally compatible salts, esters and amides.

In another preferred embodiment of the invention the SL formulation comprises as component A) quinclorac dimethylammonium, as component B) benzyl alcohol and glycol and two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac mono-[2 (2-hydroxyethoxy)-ethyl]-ammonium, as component B) benzyl alcohol and one or more additional herbicidal active ingredients.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient which is selected from is selected from clopyralid, fluoroxypyr and triclopyr, or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and one additional herbicidal active ingredient which is selected from bentazon, imazapic, imazapyr, imazaquin, imazethapyr or imazamox, or one of its environmentally compatible salts, especially bentazon or one of its environmentally compatible salts In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2 (2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients, wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]ammonium, mecoprop-P dimethylammonium and mecoprop-P mono-[2(2-hydroxyethoxy)-ethyl]ammonium.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac mono-[2 (2-hydroxyethoxy)-ethyl]-ammonium, as component B) glycol and one or more additional herbicidal active ingredients.

In another preferred embodiment of the invention the SL formulation comprises as component A) quinclorac mono-[2 (2-hydroxyethoxy)-ethyl]-ammonium, as component B) glycol and one additional herbicidal active ingredient.

In another preferred embodiment of the invention the SL formulation comprises as component A) quinclorac mono-[2 (2-hydroxyethoxy)-ethyl]-ammonium, as component B) glycol and one additional herbicidal active ingredient which is selected from 2,4-D, dichlorprop, dichlorprop-P, MCPA, mecoprop, mecoprop-P, dicamba, clopyralid, fluroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2 (2-hydroxyethoxy)-ethyl]-ammonium, as component B) glycol and one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2 (2-hydroxyethoxy)-ethyl]-ammonium, as component B) glycol and one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]ammonium, dicamba dimethylammonium, dicamba diolamine and dicamba mono-[2(2-hydroxyethoxy)-ethyl]-ammonium.

In another preferred embodiment of the invention the SL formulation comprises as component A) quinclorac mono-[2 (2-hydroxyethoxy)-ethyl]-ammonium, as component B) glycol and one additional herbicidal active ingredient which is selected from is selected from clopyralid, fluroxypyr and triclopyr, or one of its environmentally compatible salts, esters and amides.

In another preferred embodiment of the invention the SL formulation comprises as component A) quinclorac mono-[2 (2-hydroxyethoxy)-ethyl]-ammonium, as component B) glycol and one additional herbicidal active which is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium.

In another preferred embodiment of the invention the SL formulation comprises as component A) quinclorac mono-[2 (2-hydroxyethoxy)-ethyl]-ammonium, as component B) glycol and two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]ammonium, mecoprop-P dimethylammonium and mecoprop-P mono-[2(2-hydroxyethoxy)-ethyl]-ammonium.

In another preferred embodiment of the invention the SL formulation comprises as component A) quinclorac mono-[2(2-hydroxyethoxy)-ethyl]-ammonium, as component B) glycol and two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides.

In another preferred embodiment of the invention the SL formulation comprises as component A) quinclorac mono[2(2-hydroxyethoxy)-ethyl]-ammonium, as component B) glycol and two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac mono-[2(2-hydroxyethoxy)-ethyl]-ammonium, as component B) benzyl alcohol and glycol and one or more additional herbicidal active ingredients.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient which is selected from clopyralid, fluoroxypyr and triclopyr, or one of its environmentally compatible salts, esters and amides.

In another preferred embodiment of the invention the SL formulation comprises as component A) quinclorac mono-[2(2-hydroxyethoxy)-ethyl]-ammonium, as component B) benzyl alcohol and glycol and one additional herbicidal active ingredient which is selected from bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises as component A) quinclorac mono-[2(2-hydroxyethoxy)-ethyl]-ammonium, as component B) benzyl alcohol and glycol and two or more, preferably two, additional herbicidal active ingredients.

In another preferred embodiment of the invention the SL formulation comprises as component A) quinclorac mono-[2(2-hydroxyethoxy)-ethyl]-ammonium, as component B) benzyl alcohol and glycol and two or more, preferably two, additional herbicidal active ingredients wherein at least one of these additional herbicidal active ingredients is selected from 2,4-D, dichlorprop, dichlorprop-P, MCPA, mecoprop, mecoprop-P dicamba, clopyralid, fluoroxypyr, picloram and triclopyr, especially from 2,4-D, MCPA, mecoprop, mecoprop-P and dicamba or one of its environmentally compatible salts, esters and amides.

In another preferred embodiment of the invention the SL formulation comprises as component A) quinclorac mono-[2(2-hydroxyethoxy)-ethyl]-ammonium, as component B) benzyl alcohol and glycol and two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium.

In another preferred embodiment of the invention the SL formulation comprises as component A) quinclorac mono-[2(2-hydroxyethoxy)-ethyl]-ammonium, as component B) benzyl alcohol and glycol and two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and glycol and two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammmonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium.

In another preferred embodiment of the invention the SL formulation comprises as component A) quinclorac mono-[2 (2-hydroxyethoxy)-ethyl]-ammonium, as component B) benzyl alcohol and glycol and two or more, preferably two, additional herbicidal active ingredients wherein the first of the two or more, preferably two, additional herbicidal active ingredient is selected from dicamba dimethylammonium, dicamba diolamine and dicamba mono-[2(2-hydroxyethoxy)-ethyl]-ammonium, and the second of the two or more, preferably two, additional herbicidal active ingredient is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2 (2-hydroxyethoxy)-ethyl]-ammonium.

In another preferred embodiment of the invention the SL formulation comprises as component A) quinclorac mono-[2 (2-hydroxyethoxy)-ethyl]ammonium, as component B) benzyl alcohol and glycol and two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides.

In another preferred embodiment of the invention the SL formulation comprises as component A) quinclorac mono-[2 (2-hydroxyethoxy)-ethyl]-ammonium, as component B) benzyl alcohol and glycol and two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts.

In another preferred embodiment of the invention the SL formulation comprises beneath the components A) and B) one or more co-solvents.

Suitable solvents are protic solvents, like water, alcohols and polyoles, as well as dipolar aprotic solvents like ethers, ketones, lactones, carbonates, amides and lactames.

In general examples are
water;
alcohols like $C_1$-$C_8$ alkanoles such as methanol, ethanol, n-propanol, isopropanol, n-butanol, isobutanol, 2-butanol, tert.-butanol, pentanol, isoamyl alcohol, nhexanol, 1-methylpentanol, 1-ethylbutanol, n-octanol, 2-ethylhexanol and the like; $C_5$-$C_8$ cycloalkanols such as cyclopentanol, cyclohexanol and the like; polyhydric alcohols, such as sorbitol and the like; alkylene glycol monomethyl ethers such as ethylene glycol monomethyl ether, propylene glycol monomethyl ether and the like; di- and tri-$C_2$-$C_4$-alkylene glycol monomethyl ethers such asdiethylene glycol monomethyl ether, dipropylene glycol monomethyl ether and the like;
polyoles like glycerine and the like;
ethers like cyclic ethers which may contain an OH group such as tetrahydrofuran, pyran, dioxan, tetrahydrofurfurol and the like; alkylene glycol dimethyl ethers such as ethylene glycol dimethyl ether, propylene glycol dimethyl ether and the like; di- and tri-$C_2$-$C_4$-alkylene glycol dimethyl ethers such as diethylene glycol dimethyl ether, dipropylene glycol dimethyl ether and the like;
ketones, having from 3 to 8 C-atoms and optionally a hydroxyl group, such as acetone, methylethyl ketone, methylpropyl ketone, methyl-4-hydroxybutyl ketone, cyclopentanone, cyclohexanone, diaceton alcohol, mesityloxide;
lactones, having from 3 to 8 C-atoms, such as β-propiolactone, γ-butyrolactone,
carbonates, in particular dimethylcarbonat, diethylcarbonat and 2-oxa-1,3-dioxolan;
amides such as dimethylformamide, dimethylacetamid,
lactames, having preferably from 3 to 6 carbon atoms and their N-methyl and N-ethyl derivatives, such as pyrrolidin-2-one, N-methylpyrrolidin-2-one, N-ethylpyrrolidin-2-one and the like.

In a preferred embodiment of the invention the SL formulation comprises one co-solvent, especially water.

In another preferred embodiment of the invention the SL formulation comprises as component A) quinclorac dimethylammonium, as component B) benzyl alcohol and one co-solvent, especially water.

In another preferred embodiment of the invention the SL formulation comprises as component A) quinclorac mono-[2 (2-hydroxyethoxy)-ethyl]-ammonium, as component B) benzyl alcohol and one co-solvent, especially water.

In another preferred embodiment of the invention the SL formulation comprises one or more additional herbicidal active ingredients and one co-solvent, especially water.

In another preferred embodiment of the invention the SL formulation comprises as component A) quinclorac dimethylammonium, as component B) benzyl alcohol, one additional herbicidal active ingredient and one co-solvent, especially water.

In another preferred embodiment of the invention the SL formulation comprises as component A) quinclorac dimethylammonium, as component B) benzyl alcohol, one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) benzyl alcohol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, and one co-solvent, especially water.

In another preferred embodiment of the invention the SL formulation comprises as component A) quinclorac dimethylammonium, as component B) benzyl alcohol, one additional herbicidal active ingredient which is selected from clopyralid, fluoroxypyr and triclopyr, or one of its environmentally compatible salts, esters and amides, and one co-solvent, especially water.

In another preferred embodiment of the invention the SL formulation comprises as component A) quinclorac dimethylammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac dimethylammonium, as component B) benzyl alcohol, two or more, preferably two, additional herbicidal active ingredients, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein at least one is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides, and one co-solvent, especially water.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac dimethylammonium, as component B) glycol, one additional herbicidal active ingredient and one co-solvent, especially water.

In another preferred embodiment of the invention the SL formulation comprises as component A) quinclorac dimethylammonium, as component B) glycol, one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, and one co-solvent, especially water.

In another preferred embodiment of the invention the SL formulation comprises as component A) quinclorac dimethylammonium, as component B) glycol, one additional herbicidal active ingredient which is selected from clopyralid, fluoroxypyr and triclopyr, or one of its environmentally compatible salts, esters and amides, and one co-solvent, especially water.

In another preferred embodiment of the invention the SL formulation comprises as component A) quinclorac dimethylammonium, as component B) glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac dimethylammonium, as component B) glycol, two or more, preferably two, additional herbicidal active ingredients, and one co-solvent, especially water.

In another preferred embodiment of the invention the SL formulation comprises as component A) quinclorac dimethylammonium, as component B) glycol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) glycol, two or more, preferably two, additional herbicidal active ingredients wherein at least one is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, and one co-solvent, especially water.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one co-solvent, especially water.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides, and one co-solvent, especially water.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac dimethylammonium, as component B) benzyl alcohol and glycol, one additional herbicidal active ingredient and one co-solvent, especially water.

In another preferred embodiment of the invention the SL formulation comprises as component A) quinclorac dimethylammonium, as component B) benzyl alcohol and glycol, one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) benzyl alcohol and glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, and one co-solvent, especially water.

In another preferred embodiment of the invention the SL formulation comprises as component A) quinclorac dimethylammonium, as component B) benzyl alcohol and glycol, one additional herbicidal active ingredient which is selected from clopyralid, fluroxypyr and triclopyr, or one of its environmentally compatible salts, esters and amides, and one co-solvent, especially water.

In another preferred embodiment of the invention the SL formulation comprises as component A) quinclorac dimethylammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein at least one is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one co-solvent, especially water.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides, and one co-solvent, especially water.

In another preferred embodiment of the invention the SL formulation comprises as component A) quinclorac dimethylammonium, as component B) benzyl alcohol and glcol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient and one co-solvent, especially water.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]ammonium, dicamba dimethylammonium, dicamba diolamine and dicamba mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]ammonium, as component B) benzyl alcohol, one additional herbicidal active ingredient which is selected from clopyralid, fluoroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]ammonium, as component B) benzyl alcohol, two or more, preferably two, additional herbicidal active ingredients, and one co-solvent, especially water.

In another preferred embodiment of the invention the SL formulation comprises as component A) quinclorac mono-[2 (2-hydroxyethoxy)-ethyl]ammonium, as component B) benzyl alcohol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein at least one is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]ammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2 (2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, and one co-solvent, especially water.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from clopyralid, fluroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]-ammonium, as component B) glycol, one additional herbicidal active ingredient and one co-solvent, especially water.

In another preferred embodiment of the invention the SL formulation comprises as component A) quinclorac mono-[2 (2-hydroxyethoxy)-ethyl]ammonium, as component B) glycol, one additional herbicidal active ingredient which is selected from 2,4-D, dichlorprop, dichlorprop-P, MCPA, mecoprop, mecoprop-P, dicamba, clopyralid, fluroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]ammonium, dicamba dimethylammonium, dicamba diolamine and dicamba mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from clopyralid, fluroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients, and one co-solvent, especially water.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]ammonium, as component B) glycol, two or more, preferably two, additional herbicidal active ingredients wherein at least one is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]ammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac mono-[2 (2-hydroxyethoxy)-ethyl]ammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, and one co-solvent, especially water.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D, dichlorprop, dichlorprop-P, MCPA, mecoprop, mecoprop-P, dicamba, clopyralid, fluoroxypyr, picloram and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]ammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from clopyralid, fluoroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein at least one is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one co-solvent, especially water.

In another preferred embodiment of the invention the SL formulation comprises as component A) quinclorac mono-[2 (2-hydroxyethoxy)-ethyl]ammonium, as component B) benzyl alcohol and glycol, two or more, preferably two, additional herbicidal active ingredients wherein at least one is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2 (2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amides, and one co-solvent, especially water.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is bentazon, imazapic, imazapyr, imazaquin, imazethapyr or imazamox, or one of its environmentally compatible salts, especially bentazon or one of its environmentally compatible salts, and one co-solvent, especially water.

The SL formulation of the invention may also comprise one or more formulation additives, such as surfactants, defoamers, preservatives, colorants, stabilizers and the like.

Suitable surfactants are anionic surfactants such as the alkali metal salts, alkaline earth metal salts, in particular the sodium, potassium and calcium salts, and ammonium salts of
  alkylsulfonates, such as lauryl sulfonate, isotridecylsulfonate,
  alkylsulfates, in particular fatty alcohol sulfates, such as laurylsulfate, isotridecylsulfate, cetylsulfate, stearylsulfate;
  aryl- and alkylarylsulfonates, such as napthylsulfonate, dibutylnaphtylsulfonate, dodecyldiphenylether sulfonate, cumylsulfonate, nonylbenzenesulfonate, dodecylbenzene sulfonate;
  sulfonates of fatty acids and fatty acid esters;
  sulfates of fatty acids and fatty acid esters;
  sulfates of ethoxylated alkanols, such as sulfates of ethoxylated lauryl alcohol;
  sulfates of alkoxylated alkylphenols;
  alkylphosphates, $C_8$-$C_{16}$ alkylphosphates;
  dialkylphosphates, $C_8$-$C_{16}$ dialkylphosphates;
  dialkylesters of sulfosuccinic acid, such as dioctylsulfosuccinate,
  acylsarcosinates,
  fatty acids, such as stearates,
  acylglutamates,
  ligninsulfonates,
  condensates of naphthalinesulfonic acid or phenolsulfonic acid with formaldehyde;
  phosphate esters of alkoxylated alcanols or block copolymers based on EO/PO;
non-ionic surfactants, such as
  ethoxylated alkanols, in particular ethoxylated fatty alcohols and ethoxylated oxoalcohols, such as ethoxylated lauryl alcohol, ethoxylated isotridecanol, ethoxylated cetyl alcohol, ethoxylated stearyl alcohol, and esters thereof, such as acetates;
  ethoxylated alkylphenols, such as ethoxylated nonylphenyl, ethoxylated dodecylphenyl, ethoxylated isotridecylphenol and the esters thereof, e.g. the acetates;
  alkylglucosides and alkyl polygucosides;
  ethoxylated alkylglucosides;
  ethoxylated fatty amines;
  ethoxylated fatty acids;
  partial esters, such as mono-, di- and triesters of fatty acids with glycerin or Sorbitan, such as glycerin monostearate, sorbitanmonooleat, sorbitantristearate;
  ethoxylated esters of fatty acids with glycerin or sorbitan, such as ethoxylated glycerin monostearate;
  ethoxylates of vegetable oils or animal fats, such as corn oil ethoxylate, castor oil ethoxylate, tallow oil ethoxylate;
  ethoxylates of fatty amines, fatty amides or of fatty acid diethanolamides;
  alkoxylated EO/PO polymers;
and
cationic surfactants, such as
  quaterary ammonium compounds, in particular alkyltrimethylammonium salts and dialkyldimethylammonium salts, e.g. the halides, sulfates and alkylsulfates;
  pyridinium salts, in particular alkylpyridinium salts e.g. the halides, sulfates and $C_1$-$C_4$-alkylsulfates; and
  imidazolinium salts in particular N,N'-dialkylimidazolinium salts, e.g. the halides, sulfates or methoxulfates;
or mixtures thereof.

Suitable defoamers include polysiloxanes, such as polydimethyl siloxane.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof.

Suitable stabilizers comprise e.g. UV-absorbers such as cinnamic esters, 3,3-diphenyl-2-cyano acrylates, hydroxy and/or alkoxy substituted benzophenones, N-(hydroxylphenyl)-benzotriazoles, hydroxyphenyl-s-triazines, oxalic amides and salicylates, e.g. the UVINUL® 3000, 3008, 3040, 3048, 3049, 3050, 3030, 3035, 3039, 3088, UVINUL® MC80 and radical scavengers, e.g. ascorbic acid, sterically hindered amines (HALS-compounds) such as UVINUL® 4049H, 4050H and 5050H, and the like and anti-oxidants such as vitamin E.

In a preferred embodiment of the invention the SL formulation comprises one or more formulation additives, especially one surfactant. In another preferred embodiment of the invention the SL formulation comprises as component A) quinclorac dimethylammonium, as component B) benzyl alcohol and one or more formulation additives, especially one surfactant.

In another preferred embodiment of the invention the SL formulation comprises one or more additional herbicidal active ingredients and one or more formulation additives, especially one surfactant.

In another preferred embodiment of the invention the SL formulation comprises as component A) quinclorac dimethylammonium, as component B) benzyl alcohol, one additional herbicidal active ingredient and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one or more formulation additives, especially one surfactant.

In another preferred embodiment of the invention the SL formulation comprise as component A) quinclorac dimethylammonium, as component B) benzyl alcohol, one additional herbicidal active ingredient which is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac dimethylammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one or more formulation additives, especially one surfactant.

In another preferred embodiment of the invention the SL formulation comprise as component A) quinclorac dimethylammonium, as component B) benzyl alcohol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac dimethylammonium, as component B) benzyl alcohol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac dimethylammonium, as component B) glycol and one or more formulation additives, especially one surfactant.

In another preferred embodiment of the invention the SL formulation comprises as component A) quinclorac mono-[2

(2-hydroxyethoxy)-ethyl]-ammonium, as component B) benzyl alcohol and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, one or more formulation additives, especially one surfactant.

In another preferred embodiment of the invention the SL formulation comprise as component A) quinclorac mono-[2 (2-hydroxyethoxy)-ethyl]-ammonium, as component B) benzyl alcohol, one additional herbicidal active ingredient which is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac mono-[2 (2-hydroxyethoxy)-ethyl]ammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2 (2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]ammonium, mecoprop-P dimethylammonium and mecoprop-P mono-[2(2-hydroxyethoxy)-ethyl]-ammonium, and one or more formulation additives, especially one surfactant.

In another preferred embodiment of the invention the SL formulation comprise as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingedients is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac mono-[2(2-hydroxyethoxy)-ethyl]-ammonium, as component B) glycol and one or more formulation additives, especially one surfactant.

In another preferred embodiment of the invention the SL formulation comprises one or more additional herbicidal active ingredients and one or more formulation additives, especially one surfactant.

In another preferred embodiment of the invention the SL formulation comprises as component A) quinclorac dimethylammonium, as component B) glycol, one additional herbicidal active ingredient and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one or more formulation additives, especially one surfactant.

In another preferred embodiment of the invention the SL formulation comprises as component A) quinclorac dimethylammonium, as component B) glycol, one additional herbicidal active ingredient which is selected from clopyralid, fluoroxypyr and triclopyr, or one of its environmentally compatible salts, esters and amides, and one or more formulation additives, especially one surfactant.

In another preferred embodiment of the invention the SL formulation comprises as component A) quinclorac dimethylammonium, as component B) glycol, one additional herbicidal active ingredients which is selected from bentazon, imazapic, imazapyr, imazaquin, imazethapyr or imazamox, or one of its environmentally compatible salts, especially bentazon or one of its environmentally compatible salts, and one or more formulation additives, especially one surfactant.

In another preferred embodiment of the invention the SL formulation comprises as component A) quinclorac dimethylammonium, as component B) glycol, two or more, preferably two, additional herbicidal active ingredients, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one or more formulation additives, especially one surfactant.

In another preferred embodiment of the invention the SL formulation comprise as component A) quinclorac dimethylammonium, as component B) glycol, two or more, preferably two, additional herbicidal active ingredients wherein the first of the two or more, preferably two, additional herbicidal active ingredients is selected from clopyralid, fluroxypyr and triclopyr, or one of its environmentally compatible salts, esters and amids, one or more formulation additives, especially one surfactant.

In another preferred embodiment of the invention the SL formulation comprise as component A) quinclorac dimethylammonium, as component B) glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient and one or more formulation additives, especially one surfactant.

In another preferred embodiment of the invention the SL formulation comprises as component A) quinclorac mono-[2 (2-hydroxyethoxy)-ethyl]ammonium, as component B) glycol, one additional herbicidal active ingredient which is selected from 2,4-D, dichlorprop, dichlorprop-P, MCPA, mecoprop, mecoprop-P, dicamba, clopyralid, fluroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredients wherein this additional herbicidal active ingredient is selected from clopyralid, fluoroxypyr and triclopyr, or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredients wherein this additional herbicidal active ingredients is selected from bentazon, imazapic, imazapyr, imazaquin, imazethapyr or imazamox, or one of its environmentally compatible salts, especially bentazon or one of its environmentally compatible salts, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]ammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl] ammonium, and one or more formulation additives, especially one surfactant.

In another preferred embodiment of the invention the SL formulation comprise as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac dimethylammonium, as component B) benzyl alcohol and glycol, and one or more formulation additives, especially one surfactant.

In another preferred embodiment of the invention the SL formulation comprises one or more additional herbicidal active ingredients and one or more formulation additives, especially one surfactant.

In another preferred embodiment of the invention the SL formulation comprises as component A) quinclorac dimethylammonium, as component B) benzyl alcohol and glycol, one additional herbicidal active ingredient and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from clopyralid, fluroxypyr and triclopyr, or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, and one or more formulation additives, especially one surfactant.

In another preferred embodiment of the invention the SL formulation comprise as component A) quinclorac dimethylammonium, as component B) benzyl alcohol and glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac dimethylammonium, as component B) benzyl alcohol and glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol and glycol, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol and glycol, one additional herbicidal active ingredient and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from clopyralid, fluoroxypyr and triclopyr, or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, clopyralid, fluoroxypyr and triclopyr, especially from 2,4-D, MCPA, mecoprop, mecoprop-P and dicamba or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2 (2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol and glycol, two or morte, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium, and one or more formulation additives, especially one surfactant.

In another preferred embodiment of the invention the SL formulation comprise as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from clopyralid, fluoroxypyr and triclopyr, or one of its environmentally compatible salts, esters and amids, one or more formulation additives, especially one surfactant.

In another preferred embodiment of the invention the SL formulation comprise as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one or more formulation additives, especially one surfactant.

In a preferred embodiment of the invention the SL formulation comprises, one co-solvent, especially water, and one or more formulation additives, especially one surfactant.

In another preferred embodiment of the invention the SL formulation comprises as component A) quinclorac dimethylammonium, as component B) benzyl alcohol, one co-solvent, especially water, and one or more formulation additives, especially one surfactant.

In another preferred embodiment of the invention the SL formulation comprises one or more additional herbicidal active ingredients, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D, dichiorprop, dichlorprop-P, MCPA, mecoprop, mecoprop-P, triclopyr, fluoroxypyr and clopyralid, dicamba, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from triclopyr, fluoroxypyr and clopyralid, or one of its environmentally compatible salts, esters and amids, one co-solvent, especially water, and one or more formulation additives, especially one surfactant.

In another preferred embodiment of the invention the SL formulation comprises as component A) quinclorac dimethylammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients which are selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients which are selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, one additional herbicidal active ingredient, one co-solvent, especially water, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol, one additional herbicidal active ingredient which is selected from 2,4-D, dichlorprop, dichlorprop-P, MCPA, mecoprop, mecoprop-P, triclopyr, fluoroxypyr and clopyralid, dicamba, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, one additional herbicidal active ingredient which is selected from triclopyr, fluoroxypyr and clopyralid, or one of its environmentally compatible salts, esters and amids, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients which are selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2(2-hydroxyethoxy)-ethyl]ammonium, as component B) benzyl alcohol, two or more, preferably two additional herbicidal active ingredients which are selected from 2,4-D, 2,4-D dimethylammonium, 2,4-D-diethenolamine, 2,4-D-triethanolamine, 2,4-D mono-[2(2-hydroxyethoxy)-ethyl]ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, one co-solvent, especially water, and one or more formulation additives, especially one surfactant.

In another preferred embodiment of the invention the SL formulation comprises as component A) quinclorac mono-[2(2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]ammonium, mecoprop-P dimethylammonium and mecoprop-P mono-[2(2-hydroxyethoxy)-ethyl]-ammonium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac dimethylammonium, as component B) glycol, one co-solvent, especially water, and one or more formulation additives, especially one surfactant.

In another preferred embodiment of the invention the SL formulation comprises one or more additional herbicidal active ingredients, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient which is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein at least one of the herbicidal active ingredients is selected from 2,4-D, dichlorprop, dichlorprop-P, MCPA, mecoprop, mecoprop-P, dicamba, trclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein at least one of the herbicidal active ingredients is selected from selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) glycol, two or more, preferably two, additional herbicidal active ingredients wherein the first of the two or more, preferably two, herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]ammonium, dicamba potassium and dicamba sodium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein at least one of the herbicidal active ingredients is selected from 2,4-D, dichlorprop, dichlorprop-P, MCPA, mecoprop, mecoprop-P, dicamba, trclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably additional herbicidal active ingredients wherein at least one is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA potassium, MCPA sodium, MCPA ethylhexyl, MCPA mono-[2(2-hydroxyethoxy)-ethyl]-ammonium, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium, dicamba mono-[2(2-hydroxyethoxy)-ethyl]-ammonium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, and mecoprop-P potassium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine mecoprop mono-[2(2-hydroxyethoxy)-ethyl]-ammonium, mecoprop-P dimethylammonium and mecoprop-P mono-[2(2-hydroxyethoxy)-ethyl]-ammonium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) glycol, two or more, preferably two, additional herbicidal active ingredients wherein the first of the two or more, preferably two, herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac dimethylammonium, as component B) benzyl alcohol and glycol, one co-solvent, especially water, and one or more formulation additives, especially one surfactant.

In another preferred embodiment of the invention the SL formulation comprises one or more additional herbicidal active ingredients, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from 2,4-D dimethylammonium, 2,4-D-diethenolamine, 2,4-D-triethanolamine, MCPA dimethylammonium, mecoprop dimethylammonium, mecoprop diethanolamine, mecoprop-P dimethylammonium, dicamba dimethylammonium and dicamba diolamine, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from trtctbpyr, fluroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium, mecoprop-P potassium, dicamba, dicamba dimethylammonium, dicamba diolamine, dicamba potassium and dicamba sodium, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D sodium, 2,4-D 2-ethylhexyl, MCPA, MCPA dimethylammonium, MCPA potassium, MCPA sodium, MCPA ethylhexyl, MCPA thioethyl, mecoprop, mecoprop dimethylammonium, mecoprop diethanolamine, mecoprop potassium, mecoprop sodium, mecoprop-P, mecoprop-P dimethylammonium and mecoprop-P potassium, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from dicamba dimethylammonium and dicamba diolamine and the second of the two or more, preferably two, additional herbicidal active ingredients is selected from 2,4-D dimethylammonium, 2,4-D-diethenolamine, 2,4-D-triethanolamine, MCPA dimethylammonium, mecoprop dimethylammonium, mecoprop diethanolamine and mecoprop-P dimethylammonium, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac dimethylammonium, as component B) benzyl alcohol and glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D, 2,4-D dimethylammonium, 2,4-D-diethenolamine, 2,4-D-triethanolamine, 2,4-D sodium, 2,4-D 2-ethylhexyl, 2,4-D mono-[2 (2-hydroxyethoxy)-ethyl]-ammonium, MCPA, MCPA dimethylammonium, MCPA mono-[2(2-hydroxyethoxy)ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium, mecoprop-P mono-[2(2-hydroxyethoxy)-ethyl]-ammonium, dicamba dimethylammonium, dicamba diolamine and dicamba mono-[2(2-hydroxyethoxy)-ethyl]-ammonium, one co-solvent, especially water, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol and glycol, one additional herbicidal active ingredient which is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, one additional herbicidal active ingredient which is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

In another preferred embodiment of the invention the SL formulation comprises as component A) quinclorac mono-[2 (2-hydroxyethoxy)-ethyl]ammonium, as component B) benzyl alcohol and glycol, two or more, preferably two, additional herbicidal active ingredients, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein at least one of these additional herbicidal active ingredients is selected from 2,4-D, dichlorprop, dichlorprop-P, MCPA, mecoprop, mecoprop-P, dicamba, triclopyr, fluoroxypyr and clopyralid, especially from 2,4-D, MCPA, mecoprop, mecoprop-P and dicamba or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein at least one of these additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2(2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium, mecoprop-P potassium, dicamba, dicamba dimethylammonium, dicamba diolamine, dicamba mono-[2(2-hydroxyethoxy)-ethyl]-ammonium, dicamba potassium and dicamba sodium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is dicamba or one of its environmentally compatible salts, esters and amides and the second of the two or more, preferably two, additional herbicidal active ingredients is selected from 2,4-D, dichlorprop, dichlorprop-P, MCPA, mecoprop and mecoprop-P, especially from 2,4-D, MCPA, mecoprop and mecoprop-P or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from dicamba, dicamba dimethylammonium, dicamba diolamine, dicamba mono-[2(2-hydroxyethoxy)-ethyl]ammonium, dicamba potassium and dicamba sodium and the second of the two or more, preferably two, additional herbicidal active ingredients is selected from 2,4-D, 2,4-D dimethylammonium, 2,4-D-diethenolamine, 2,4-D-triethanolamine, 2,4-D mono-[2(2-hydroxyethoxy)-ethyl]-ammonium, 2,4-D sodium, 2,4-D 2-ethylhexyl, MCPA, MCPA dimethylammonium, MCPA mono-[2(2-hydroxyethoxy)-ethyl]-ammonium, MCPA potassium, MCPA sodium, MCPA ethylhexyl, MCPA thioethyl, mecoprop, mecoprop dimethylammonium, mecoprop diethanolamine, mecoprop mono-[2 (2-hydroxyethoxy)-ethyl]-ammonium, mecoprop potassium, mecoprop sodium, mecoprop-P, mecoprop-P dimethylammonium, mecoprop-P mono-[2(2-hydroxyethoxy)-ethyl]-ammonium and mecoprop-P potassium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from dicamba dimethylammonium, dicamba diolamine and dicamba mono-[2(2-hydroxyethoxy)-ethyl]-ammonium, and the second of the two or more, preferably two, additional herbicidal active ingredients is selected from 2,4-D dimethylammonium, 2,4-D-diethenolamine, 2,4-D-triethanolamine, 2,4-D mono-[2(2-hydroxyethoxy)-ethyl]-ammonium, MCPA dimethylammonium, MCPA mono-[2(2-hydroxyethoxy)-ethyl]-ammonium, mecoprop dimethylammonium, mecoprop diethanolamine, mecoprop mono-[2(2-hydroxyethoxy)-ethyl]-ammonium, mecoprop-P dimethylammonium and mecopop-P mono-[2(2-hydroxyethoxy)-ethyl]ammonium, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from triclopyr, fluoroxypyr and clopyralid, or one of its environmentally compatible salts, esters and amides, one co-solvent, especially water, and one or more formulation additives, especially one surfactant.

In another preferred embodiment of the invention the SL formulation comprises as component A) quinclorac mono-[2 (2-hydroxyethoxy)-ethyl]-ammonium, as component B) benzyl alcohol and glycol, two or more, preferably two, additional herbicidal active ingredients wherein the first of the two or more, preferably two, additional herbicidal active ingredients is selected from bentazon, imazapic, imazapyr, imazaquin, imazethapyr or imazamox, or one of its environmentally compatible salts, especially bentazon or one of its environmentally compatible salts, one co-solvent, especially water, and one or more formulation additives, especially one surfactant.

The amount of the quinclorac ammonium salt of formula I in the SL formulation of the invention usually ranges from 1 to 40% by weight, preferably from 5 to 30% by weight and in particular from 10 to 20% by weight based on the total weight of said formulation.

The amount of the solvent of formula IIa and/or IIb in the SL formulation of the invention usually ranges from 10 to 95% by weight, preferably from 20 to 70% by weight and in particular from 30 to 60% by weight based on the total weight of said formulation.

The SL formulation of the present invention may also comprise one or more additional herbicidal active ingredients, especially in an amount from 1 to 40% by weight, preferably from 2 to 30% by weight and in particular from 2 to 25% by weight (based on the total weight of said formulation).

The SL formulation of the present invention may also comprise one or more co-solvents, especially in an amount from 10 to 90% by weight, preferably from 30 to 60% by weight and in particular from 40 to 50% by weight based on the total weight of said formulation.

The SL formulation of the present invention may also comprise one or more formulation additives, especially in an amount from 0.1 to 20% by weight based on the total weight of said formulation.

The SL formulation according to the present invention can be prepared by adding the quinclorac ammonium salt of formula I and if desired, the additional herbicidal active ingredient(s), co-solvent(s) and/or formulation additive(s) to the solvent of formula IIa and/or IIb, while stirring, and, optionally while heating.

It is also possible that some of the components of the SL formulation are premixed and the remaining components are added thereafter while stirring, and, optionally while heating.

In another embodiment the SL formulation can be prepared by mixing together quinclorac "acid", an amine of formula III $$NR^1R^2R^3 \qquad (III)$$

wherein the meaning of $R^1$, $R^2$ and $R^3$ are those given for the quinclorac ammonium salt of formula I,
and, if desired one or more additional herbicidal active ingredients and/one or more solvents and/or one or more formulation additives, wherein the amounts of quinclorac "acid" and of the amine of formula III are from 0.8:1 to 1.2:1 mol %, and the amounts of other components are as desired.

Especially quinclorac "acid" and the amine of formula III are used in equimolar amounts.

In case one of the additional herbicidal active ingredients is also used in its $[NR_1R_2R_3H]^+$ form the respective "neutral form" of the additional herbicidal active ingredient may be mixed together with the other components as mentioned above and an additional respective amount of the amine of formula III, which is in the range of from 0.8:1 to 1.2:1 mol %.

In a preferred embodiment the additional herbicidal active ingredient and the additional amount of amine of formula III are used in an equimolar ratio.

In a special embodiment the amine of formula III is used as aqueous solution.

If desired, the additional herbicidal active ingredients and the formulation additives may be contained within the SL formulation of the present invention. However, it is also possible to add these components after dilution with water to the ready-to-use aqueous composition.

Upon dilution with water, the SL formulation of the invention forms an aqueous herbicide composition which comprises a quinclorac ammonium salt of formula I, a solvent of formula IIa and/or IIb, water and optionally one or more additional herbicidal active ingredients, and/or one or more co-solvents and/or one or more formulation additives.

In order to obtain these aqueous herbicide compositions, the SL formulation of the invention are usually diluted with at least 1. parts of water, preferably at least 20 parts of water, in particular at least 40 parts of water and more preferably at least 80 parts of water (all parts are given in parts by weight) (based on the total weight of the aqueous herbicide compositions).

Dilution will be usually achieved by pouring the SL formulations of the invention into water. Usually, dilution is achieved with agitation, e.g. with stirring, to ensure a rapid mixing of the concentrate in water. However, agitation is not necessary. Though the temperature of mixing is not critical, mixing is usually performed at temperatures ranging from 0 to 100° C., in particular from 10 to 50° C. or at ambient temperature.

The water used for mixing is usually tap water. However the water may already contain further compounds which are used in plant protection, e.g. nutrificants, fertilizers, water soluble pesticides or alkylates of vetetable oils, such as methylated seed oil (MSO), preferably MSO. It is also possible that the SL formulation is mixed with water and if desired one or more of said further compounds which are used in plant protection, e.g. nutrificants, fertilizers, water soluble pesticides or alkylates of vetetable oils, such as methylated seed oil (MSO), are added.

If desired, MSO is employed in amounts from 0.125 to 5% by volume, preferably from 0.25 to 2.5% by volume and in particular from 0.5 to 1% by volume (based on the total volume of the aqueous herbicide compositions=final volume for application).

The aqueous herbicide compositions of the invention can be used as such to control undesired vegetation. Therefore, the present invention also relates to an aqueous herbicide composition which is obtained by diluting the SL formulation of the present invention with water and optionally with further compounds which are used in plant protection, e.g. nutrificants, fertilizers, water soluble pesticides or alkylates of vetetable oils, such as methylated seed oil (MSO).

In a preferred embodiment of the aqueous herbicide compositions the SL formulation is diluted with water only.

In a further preferred embodiment of the aqueous herbicide compositions the SL formulation is diluted with water and alkylates of vetetable oils, especially MSO.

In a further preferred embodiment of the aqueous herbicide compositions the SL formulation is diluted with water and alkylates of vetetable oils, especially MSO, only.

The present invention also relates to the use of said aqueous herbicide compositions for control of undesired vegetation by contacting the undesired plants, their habitat and/or their seeds with an effective amount of an aqueous herbicidal composition as described herein.

The compositions of the invention after dilution are applied by usual means which are familiar to a skilled person.

Usually the application rate of the quinclorac ammonium salt of formula I, calculated on the basis of the quinclorac "acid", is in the range of 280 to 1680 g ai/ha, preferably 420 to 1400 g ai/ha.

Usually the application rate of mecoprop or mecoprop-P, its salts, esters and/or amids, calculated on the basis of the mecoprop "acid" and mecoprop-P "acid", respectively, is in the range of 210 to 1260 g ai/ha, preferably 420 to 840 g ai/ha.

Usually the application rate of 2,4-D, its salts, esters and/or amids, calculated on the basis of the 2,4-D "acid", is in the range of 420 to 1680 g ai/ha, preferably 600 to 1400 g ai/ha.

Usually the application rate of MCPA, its salts, esters and/or amids, calculated on the basis of the MCPA "acid", is in the range of 420 to 1680 g ai/ha, preferably 600 to 1400 g ai/ha.

Usually the application rate of dicamba, its salts, esters and/or amids, calculated on the basis of the dicamba "acid", is in the range of 30 to 400 g ai/ha, preferably 50 to 250 g ai/ha.

A SL formulation represents a liquid, homogeneous formulation. Usually the active ingredient(s) of the SL formulation is/are dissolved in water or a combination of water and suitable water soluble solvent(s) plus optionally other ingredients. The dilution of a SL formulation with water results in a clear solution.

The present invention also relates to compounds of formula I and preferred embodiments thereof as mentioned above.

The compounds of formula I can be prepared by mixing together quinclorac "acid" and an amine of formula III

$$NR^1R^2R^3 \quad (III)$$

wherein the meaning of $R^1$, $R^2$ and $R^3$ are those given for the quinclorac ammonium salt of formula I. The reaction may be performed in substance or in an appropriate solvent, for example water, an alcohol, like methanol and ethanol, a ketone, like acetone, diethylketone.

The following examples are intended to further illustrate the present invention.

A. Preparation of the SL Formulations of the Invention

EXAMPLE 1

A SL formulation containing 20% ai (active ingredient) of quinclorac was prepared by blending 10.4 g of quinclorac "acid" (98% tech) 34.6 g benzyl alcohol and 5.0 g of a 40% by weight aqueous solution of dimethylamine. Mixing of said components at room temperature produced a clear homogeneous solution containing 69.2% benzyl alcohol and 23.7% quinclorac dimethylammonium salt.

COMPARISON EXAMPLE 1*

A formulation containing 20% ai of quinclorac prepared by blending 10.4 g of quinclorac "acid" (98% tech) and 39.6 g benzyl alcohol failed to produce a clear homogeneous solution.

COMPARISON EXAMPLE 1**

A formulation containing 16.7% ai of quinclorac prepared by blending 17.0 g of quinclorac "acid" (98% technical), 73.5 g of water and 9.5 g a 40% by weight aqueous solution of dimethylamine failed to produce a clear homogeneous solution.

EXAMPLE 2

A SL formulation containing 30% ai of quinclorac was prepared by blending 15.6 g of quinclorac "acid" (96% technical), 26.9 g of benzyl alcohol and 7.5 g of a 40% by weight aqueous solution of dimethylamine. Mixing of said components at room temperature produced a clear homogeneous solution containing 53.75% benzyl alcohol and 35.5% quinclorac dimethylammonium salt.

EXAMPLE 3

A SL formulation containing 15.4% ai quinclorac, 15.4% ai 2,4-D and 2% ai dicamba was prepared by blending 47.1 g of quinclorac "acid" (98% technical), 48.9 g 2,4-D "acid" (94.7% technical), 114 g of benzyl alcohol and 24 g of water to form slurry. 51 g of a 40% by weight aqueous solution of dimethylamine was then added and mixed until a clear homogeneous solution is formed. 15.0 g of dicamba DMA salt, as a 40% ai aqueous solution was then added and mixed together at room temperature to form a clear homogeneous solution containing 38% benzyl alcohol.

EXAMPLE 4

A SL formulation containing 15.4% ai quinclorac, 15.4% ai MCPA and 2% ai dicamba was prepared by blending 47.1 g of quinclorac "acid" (98% technical), 46.8 g MCPA "acid" (98.5% technical), 118.2 g of benzyl alcohol and 24 g of water to form a slurry. 48.9 g of a 40% by weight aqueous solution of dimethylamine was then added and mixed until a clear homogeneous solution is formed. 15.0 g of dicamba DMA salt, as a 40% ai aqueous solution, was then added and mixed together at room temperature to form a clear homogeneous solution containing 39.4% benzyl alcohol.

EXAMPLE 5

An SL formulation containing 16.2% ai quinclorac, 12% ai of mecoprop-P and 2.2% ai dicamba was prepared as follows. 190.0 g of a 40% by weight aqueous solution of dimethylamine was added to 120 g of water and mixed. 30.0 g of dicamba "acid" (95% tech), 198 g of quinclorac "acid" (98% tech) and 151.0 g of mecoprop-P "acid" (95.1% tech) were then added and mixed. 501 g of benzyl alcohol was then added and mixed for ten minutes. An additional 7.6 g of a 40% by weight aqueous solution of dimethylamine was then added and mixed until a clear solution was formed at a final pH of 9.5. 2.4 g of water was then added to bring final batch size to 1200 grams. The final formulation was a clear homogeneous solution containing 41.7% benzyl alcohol.

EXAMPLE 6

An SL formulation containing 16% ai quinclorac, 8% ai of mecoprop-P and 2.1% ai dicamba was prepared as follows. 300 g of a 40% by weight aqueous solution of dimethylamine was added to 300 g of water and mixed. 53.9 g of dicamba "acid" (95% tech), 388.9 g of quinclorac "acid" (98.9% tech) and 201.8 g of mecoprop-P "acid" (95.1% tech) were then added and mixed. 528 g of benzyl alcohol and 528 g of ethylene glycol were then added and mixed for ten minutes. An additional 62.7 g of a 40% by weight aqueous solution of dimethylamine was then added and mixed until a clear solution was formed at a final pH of 9.5. 16.8 g of water was then added to bring final batch size to 2400 grams. The final formulation was a clear homogeneous solution contained 22% benzyl alcohol and 22% ethylene glycol.

EXAMPLE 7

As SL formulation containing 12% ai quinclorac, 6% ai mecoprop-P, 1.6% ai dicamba and 9.7% ai 2,4-D was prepared by blending 75 g of the SL formulation prepared in Example 6 with 25 g of 2,4-D DMA salt, as a 38.9% ai aqueous solution. The final formulation was a clear homogeneous solution containing 16.5% benzyl alcohol and 16.5% ethylene glycol.

EXAMPLE 8

When diluted in water at 3 g/100 ml of water the SL formulations obtained according to Examples 1 to 7 gave a clear homogeneous solution.

B. Biological Tests

EXAMPLE 9

Large crabgrass seedlings were cultured in a standard growth media in 9 cm pots (one plant per pot) and allowed to develop under greenhouse conditions to the 1 to 3 tiller growth stage. Prior to herbicide application, a one centimeter vermiculite barrier was placed in the pots. Quinclorac treatments were applied at rates of 420 g ai/ha) and 840 g ai/ha. All treatments included a methylated seed oil adjuvant @ 0.5% v/v of finished spray volume. Treatments were applied with a standard track sprayer using an even flat fan spray nozzle calibrated to apply a spray volume of 374 l/ha. The vermiculite barrier was removed immediately after the spray applications were made. The crabgrass plants were then maintained under greenhouse conditions and subirrigated for the remainder of the experiment. The formulations according to the present invention have been compared with the standard acid formulation sold under the tradename DRIVE 75 (a 75% dry flowable) on large crabgrass (*Digitaria sanguinalis*). Nineteen days after herbicide treatment, herbicide effects were visually assessed on a 0-100% control scale (0=no effect; 100=complete death).

TABLE 1

Herbicidal action of quinclorac dimethylammonium = salt a, benzyl alcohol and methylated seed oil (MSO) 19 days after post-emergence treatment

| | Application rate [g/ha ai] | *Digitaria sanguinalis* Damage [%] |
|---|---|---|
| salt a + benzyl alcohol + MSO | 420 + 1155 + 0.5% v/v | 81 |
| Comparison DRIVE 75 + MSO | 420 + 0.5% v/v | 20 |

TABLE 2

Herbicidal action of quinclorac dimethylammonium = salt a, benzyl alcohol or glycol, and methylated seed oil (MSO) 19 days after post-emergence treatment

| | Application rate [g/ha ai] | *Digitaria sanguinalis* Damage [%] |
|---|---|---|
| salt a + glycol + MSO | 840 2635 0.5% v/v | 92 |
| salt a + benzyl alcohol + MSO | 840 2310 0.5% v/v | 99 |
| Comparison DRIVE 75 + MSO | 840 + 0.5% v/v | 20 |

The data listed in Tables 1 and 2 show that at both tested rates (420 and 840 g ai/ha), salt a+benzyl alcohol or glycol provided significantly better foliar control of large crabgrass than the standard commercial acid formulation.

EXAMPLE 10

Large crabgrass seedlings were cultured in a standard growth media in 9 cm pots (one plant per pot) and allowed to development under greenhouse conditions to the 1 to 2 tiller growth stage. Treatments consisted of an untreated control, the formulation according to the present invention and DRIVE 75 DF herbicide applied at 840 g ai/ha with and without methylated seed oil adjuvant @ 0.5% v/v of finished spray volume. Prior to herbicide application, a one centimeter vermiculite barrier was placed in the pots. Treatments were applied with a standard track sprayer using an even flat fan spray nozzle calibrated to apply a spray volume of 374 l/ha. The vermiculite barrier was removed immediately after spray applications were made. To evaluate foliar absorption effects, treated plants were washed with deionized water+surfactant solution at 0, 4 and 24 hrs after treatment to remove any herbicide from the plant leaf surface that was not absorbed. The crabgrass plants were then maintained under greenhouse conditions and subirrigated for the remainder of the experiment. Nine days after herbicide treatment, herbicide effects were visually assessed on a 0-100% control scale (0=no effect; 100=complete death). The results are summerized in Tables 3 and 4 wherein quinclorac dimethylammonium=salt a.

TABLE 3

| | Application rate [g ai/ha] | *Digitaria sanguinalis* Damage [%] Time between application and wash off [h] | | |
|---|---|---|---|---|
| | | immediately | 4 | 24 |
| Comparison DRIVE 75 | 840 | 5 | 10 | 20 |
| Salt a + benzyl alcohol | 840 + 2310 | 30 | 40 | 60 |

TABLE 4

| | Application rate [g ai/ha] | *Digitaria sanguinalis* Damage [%] Time between application and wash off [h] | | | |
|---|---|---|---|---|---|
| | | immediately | 2 | 4 | 24 |
| Comparison DRIVE 75 + MSO | 840 + 0.5% v/v | 10 | 20 | 40 | 30 |
| Salt a + benzyl alcohol + MSO | 840 + 2310 + 0.5% v/v | 30 | 90 | 95 | 98 |

The data listed in Tables 3 and 4 show that across wash off timings, the formulation according the present invention provided better crabgrass control than the standard acid.

We claim:

1. A soluble liquid (SL) formulation comprising
A) a quinclorac ammonium salt of formula I

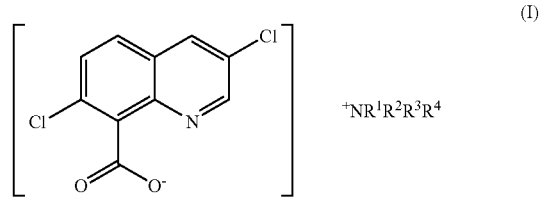

wherein
$R^1$, $R^2$, $R^3$ and $R^4$ are independently hydrogen or $C_1$-$C_6$-alkyl;
and
B) a solvent of formula IIa

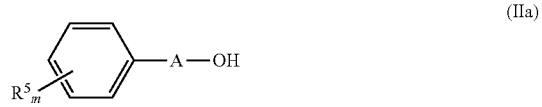

wherein
$R^5$ is $C_1$-$C_6$-alkyl;
A is $C_1$-$C_6$-alkylene or $C_1$-$C_6$-oxyalkylene;
m is 0, 1, 2 or 3;
and/or
a solvent of formula IIb

wherein
B is a straight-chain or branched $C_2$-$C_8$-alkylene or $C_2$-$C_4$-alkyleneoxy-$C_2$-$C_4$ alkylene or $C_2$-$C_3$-alkyleneoxy-$C_2$-$C_3$-alkyleneoxy-$C_2$-$C_3$-alkylene.

2. The SL formulation according to claim 1 wherein
$R^1$ is hydrogen or $C_1$-$C_6$-alkyl;
$R^2$, $R^3$ are independently $C_1$-$C_6$-alkyl; and
$R^4$ is hydrogen.

3. The SL formulation according to claim 1 wherein
$R^1$, $R^4$ are hydrogen; and
$R^2$, $R^3$ are independently $C_1$-$C_6$-alkyl.

4. The SL formulation according to claim 1 wherein the quinclorac ammonium salt of formula (I) is quinclorac dimethylammonium.

5. The SL formulation according to claim 1 comprising as component B a solvent of formula IIa or a solvent of formula IIb.

6. The SL formulation according to claim 5 wherein the solvent is a solvent of formula IIa.

7. The SL formulation according to claim 1 wherein m is 0.

8. The SL formulation according to claim 1 wherein A is methylene, ethylene or oxyethylene.

9. The SL formulation according to claim 6 wherein the solvent of formula IIa is benzyl alcohol.

10. The SL formulation according to claim 5 wherein the solvent is a solvent of formula IIb.

11. Previously presented): The SL formulation according to claim 1 wherein B is a straight-chain or branched $C_2$-$C_8$-alkylene.

12. The SL formulation according to claim 1 wherein the solvent is ethylene glycol or propylene glycol.

13. The SL formulation according to claim 1 wherein B is a straight-chain or branched $C_2$-$C_4$-alkyleneoxy-$C_2$-$C_4$-alkylene or $C_2$-$C_3$-alkyleneoxy-$C_2$-$C_3$-alkyleneoxy-$C_2$-$C_3$-alkylene.

14. The SL formulation according to claim 1 comprising as component B a solvent of formula IIa and a solvent of formula IIb.

15. The SL formulation according to claim 1 comprising from about 1 to 40% by weight, based on the total weight of said formulation, of a quinclorac ammonium salt of formula (I).

16. The SL formulation according to claim 1 comprising from about 10 to about 95% by weight, based on the total weight of said formulation, a solvent of formula IIa and/or a solvent of formula IIb.

17. The SL formulation according to claim 1 further comprising one or more additional herbicidal active ingredients.

18. The SL formulation according to claim 17 wherein said one or more additional herbicidal active ingredients are selected from the group consisting of clomeprop, 2,4-D, 2,4-DB, dichlorprop, dichlorprop-P, MCPA, MCPB, mecoprop, mecoprop-P, 2,4,5-T, chloramben, dicamba, 2,3,6-TBA, tricamba, clopyralid, fluoroxypyr, picloram, trichlopyr or benazolin or one of its environmentally compatible salts, esters or amides, bentazon, imazapic, imazapyr, imazaquin, imazethapyr and imazamox, or an environmentally compatible salt thereof.

19. The SL formulation according to claim 17 comprising one additional active ingredient which is selected from the group consisting of dicamba, 2,4-D, dichlorprop, dichlorprop-P, MCPA, mecoprop, mecoprop-P, triclopyr, fluoroxypyr or clopyralid or one of its environmentally compatible salts, esters or amides, bentazon, imazapic, imazapyr, imazaquin, imazethapyr and imazamox, or one of its environmentally compatible salts.

20. The SL formulation according to claim 18 wherein said one or more additional active ingredients are selected from the group consisting of dicamba, 2,4-D, dichlorprop, dichlorprop-P, MCPA, mecoprop and mecoprop-P or one of its environmentally compatible salts, esters or amides thereof.

21. The SL formulation according to claim 18 wherein said one or more additional herbicidal active ingredients are selected from the group consisting of triclopyr, fluoroxypyr and clopyralid or environmentally compatible salts, esters or amids thereof.

22. The SL formulation according to claim 18 wherein said one or more additional herbicidal active ingredients are selected from the group consisting of bentazon, imazapic, imazapyr, imazaquin, imazethapyr, and imazamox or an environmentally compatible salt thereof.

23. The SL formulation according to claim 17 comprising from about 1 to about 40% by weight, based on the total weight of the formulation, of said additional herbicidal active ingredient(s).

24. The SL formulation according to claim 1 further comprising one or more co-solvents.

25. The SL formulation according to claim 24 wherein said co-solvent is water.

26. The SL formulation according to claim 25 comprising from about 10 to about 90% by weight, based on the total weight of the formulation, of said co-solvent(s).

27. The formulation according to claim 1 further comprising one or more formulation additives.

28. The formulation according to claim 27 comprising from about 0.1 to about 20% by weight, based on the total weight of the formulation, of said formulation additive(s).

29. The SL formulation obtainable by mixing together quinclorac "acid", an amine of formula III, $$NR^1R^2R^3 \qquad (III)$$

wherein the meaning of $R^1$, $R^2$ and $R^3$ are given in claim 1, and a solvent of formula IIa and/or a solvent of formula IIb as defined in claim 1, and optionally one or more additional herbicidal active ingredients and/or one or more co-solvents and/or one or more formulation additives.

30. An aqueous herbicide composition obtainable by mixing the SL formulation of claim 1 with water and optionally with further compounds which are used in plant protection.

31. A method for controlling undesirable vegetation, which comprises diluting a herbicidally active amount of a soluble liquid (SL) formulation comprising A) a quinclorac ammonium salt of formula I

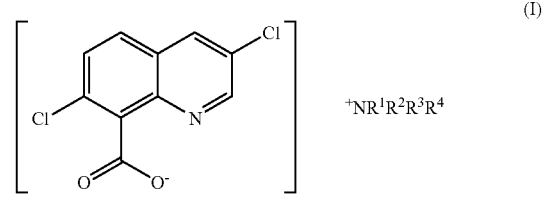

wherein
$R^1$, $R^2$, $R^3$ and $R^4$ are independently hydrogen or $C_1$-$C_6$-alkyl;
and
B) a solvent of formula IIa

wherein
$R^5$ is $C_1$-$C_6$-alkyl;
A is $C_1$-$C_6$-alkylene or $C_1$-$C_6$-oxyalkylene;
m is 0, 1, 2 or 3;
and/or
a solvent of formula IIb $$HO-B-OH \qquad (IIb)$$

wherein
B is a straight-chain or branched $C_2$-$C_8$-alkylene or $C_2$-$C_4$-alkyleneoxy-$C_2$-$C_4$-alkylene or $C_2$-$C_3$-alkyleneoxy-$C_2$-$C_3$-alkyleneoxy-$C_2$-$C_3$-alkylene with water, and contacting said diluted formulation with plants, their habitat and/or their seeds.

32. The method of claim 31 wherein the diluted formulation further contains an alkylated vegetable oil.

33. The method of claim 31 wherein the diluted formulation further contains methylated seed oil.

* * * * *

UNITED STATES PATENT AND TRADEMARK OFFICE
CERTIFICATE OF CORRECTION

PATENT NO. : 8,778,840 B2  
APPLICATION NO. : 12/669198  
DATED : July 15, 2014  
INVENTOR(S) : Rainer Berghaus et al.

Page 1 of 1

It is certified that error appears in the above-identified patent and that said Letters Patent is hereby corrected as shown below:

In the Claims,

Claim 18, col. 77, line 39, delete "fluoroxypyr" and insert therefore --fluroxypyr--.

Claim 19, col. 77, lines 47-48, delete "fluoroxypyr" and insert therefore --fluroxypyr--.

Claim 21, col. 77, line 60, delete "fluoroxypyr" and insert therefore --fluroxypyr--.

Signed and Sealed this  
Thirtieth Day of June, 2015

Michelle K. Lee  
*Director of the United States Patent and Trademark Office*